United States Patent
Jones et al.

(10) Patent No.: US 7,582,101 B2
(45) Date of Patent: Sep. 1, 2009

(54) HEATED MECHANICAL DETACHMENT FOR DELIVERY OF THERAPEUTIC DEVICES

(75) Inventors: Donald K. Jones, Lauderhill, FL (US); Vladimir Mitelberg, Aventura, FL (US)

(73) Assignee: Cordis Development Corporation, Miami Lakes, FL (US)

( * ) Notice: Subject to any disclaimer, the term of this patent is extended or adjusted under 35 U.S.C. 154(b) by 599 days.

(21) Appl. No.: 11/363,775

(22) Filed: Feb. 28, 2006

(65) Prior Publication Data
US 2007/0203518 A1    Aug. 30, 2007

(51) Int. Cl.
*A61M 29/00* (2006.01)
(52) U.S. Cl. .............. 606/200; 606/195; 604/93.01
(58) Field of Classification Search ............ 606/200; 623/1.11, 1.18
See application file for complete search history.

(56) References Cited

U.S. PATENT DOCUMENTS

| | | | |
|---|---|---|---|
| 5,108,407 A | 4/1992 | Geremia et al. | |
| 5,224,954 A | 7/1993 | Watts et al. | |
| 5,250,071 A | 10/1993 | Palermo | |
| 5,520,697 A | 5/1996 | Lindenberg et al. | |
| 5,578,074 A | 11/1996 | Mirigian | |
| 5,746,769 A | 5/1998 | Ton et al. | |
| 5,814,062 A | 9/1998 | Sepetka | |
| 5,895,391 A | 4/1999 | Farnholtz | |
| 5,911,737 A | 6/1999 | Lee | |
| 5,989,242 A | 11/1999 | Saadat et al. | |
| 6,102,917 A | 8/2000 | Maitland et al. | |
| 6,102,933 A | 8/2000 | Lee et al. | |
| 6,149,664 A * | 11/2000 | Kurz ....................... | 606/194 |
| 6,165,198 A | 12/2000 | McGurk et al. | |
| 6,238,415 B1 | 5/2001 | Sepetka | |
| 6,277,125 B1 | 8/2001 | Barry | |
| 6,296,622 B1 | 10/2001 | Kurz et al. | |
| 6,723,108 B1 | 4/2004 | Jones et al. | |
| 6,849,081 B2 | 2/2005 | Sepetka et al. | |
| 2003/0176877 A1 * | 9/2003 | Narciso, Jr. ............. | 606/153 |
| 2004/0106933 A1 | 6/2004 | Barry | |
| 2004/0172053 A1 * | 9/2004 | Barry et al. ............ | 606/195 |
| 2004/0204701 A1 | 10/2004 | Cox | |
| 2005/0113864 A1 | 5/2005 | Gandhi et al. | |
| 2005/0149108 A1 | 7/2005 | Cox | |

OTHER PUBLICATIONS

European Search Report in EP 07 25 0697, dated Jul. 7, 2007.

* cited by examiner

*Primary Examiner*—Todd E Manahan
*Assistant Examiner*—Leander Taylor, III
(74) *Attorney, Agent, or Firm*—Cook Alex Ltd.

(57) ABSTRACT

The disclosure describes apparatuses and methods for the luminal delivery of therapeutic devices. The apparatus includes a decoupling assembly comprising a retention element, a energy-responsive element and a thermally sensitive element. The application of heat to the thermally sensitive element alters its configuration such that it no longer maintains the retention element in engagement with the therapeutic device, releasing the therapeutic device.

30 Claims, 2 Drawing Sheets

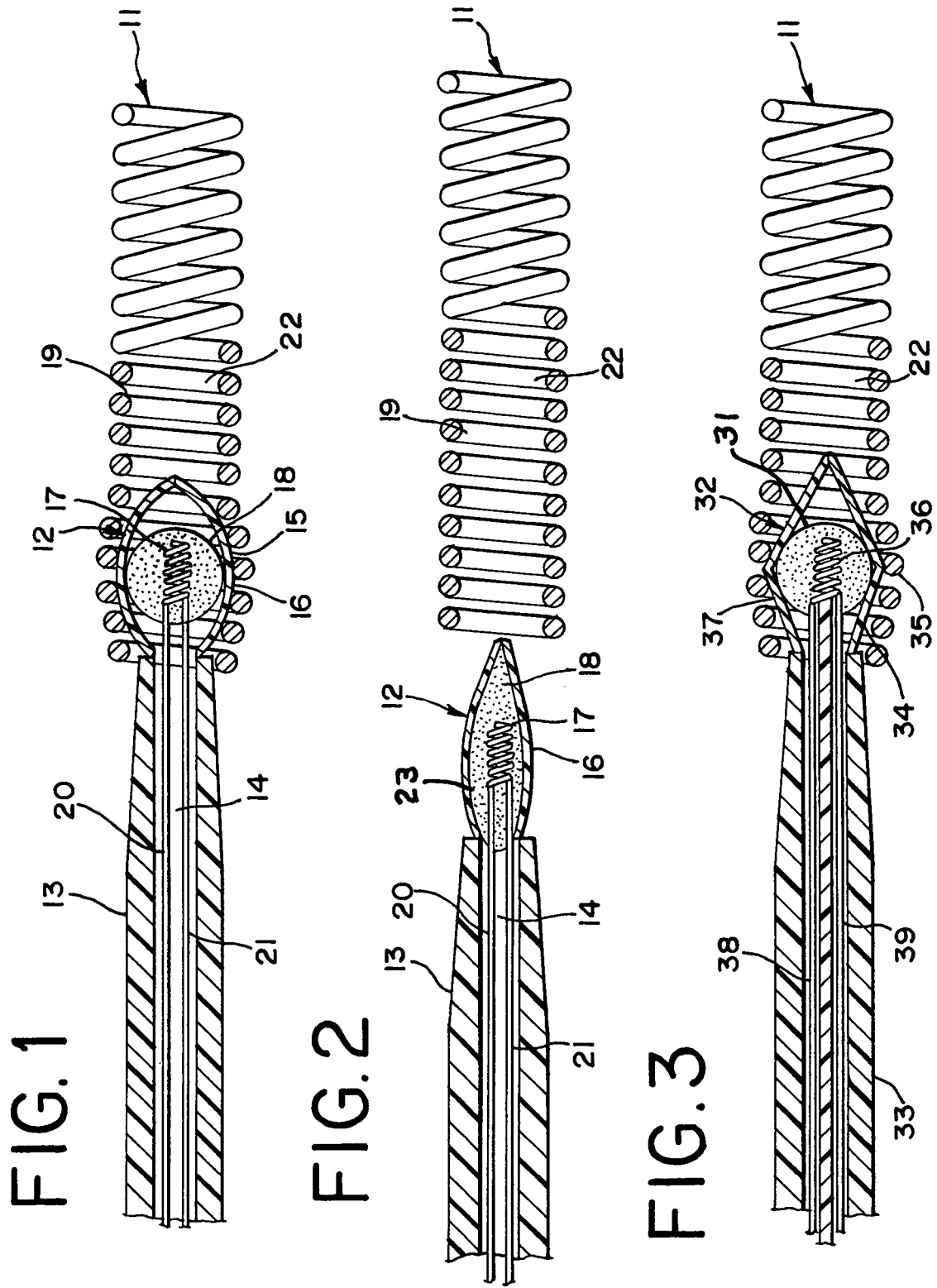

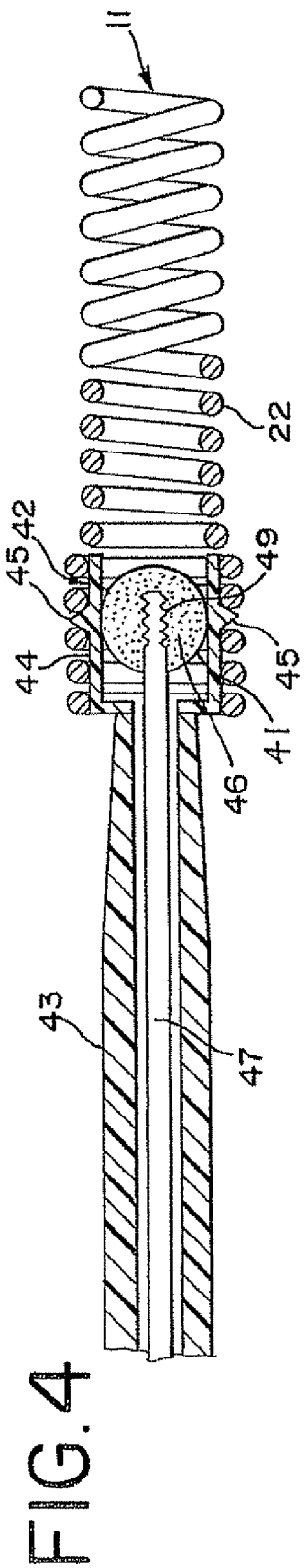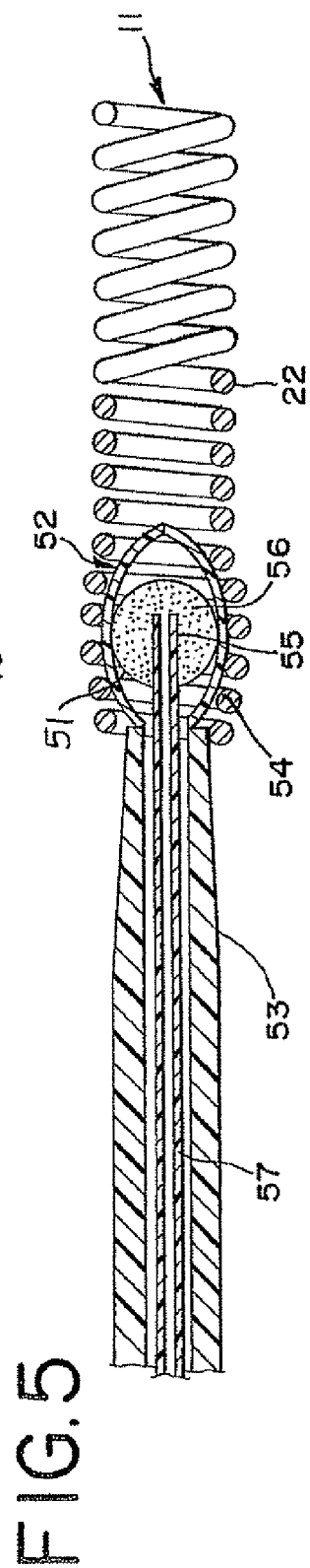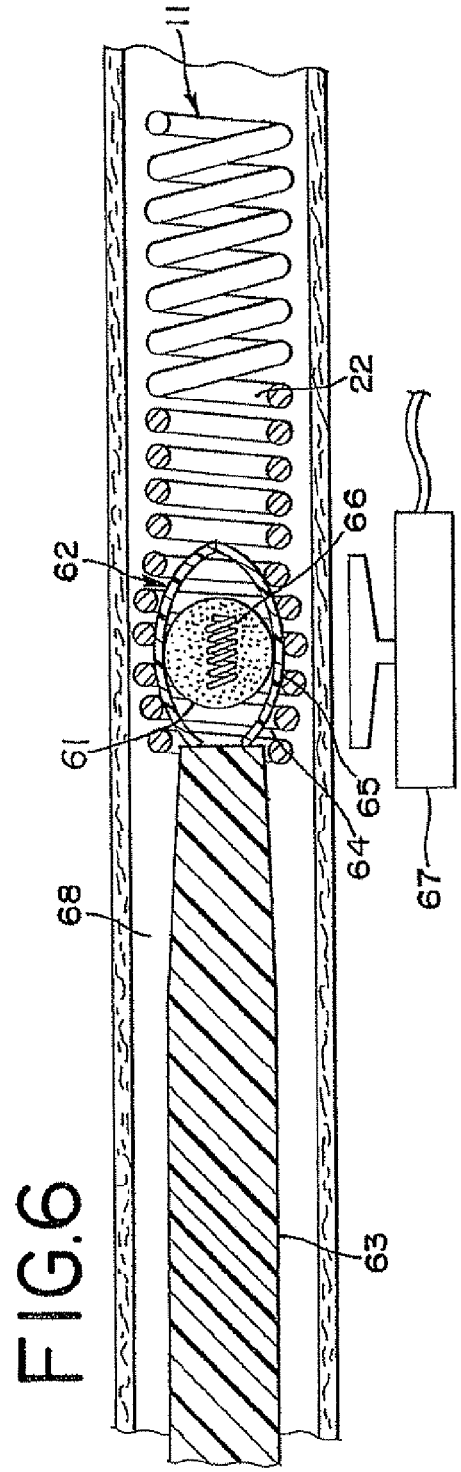

HEATED MECHANICAL DETACHMENT FOR DELIVERY OF THERAPEUTIC DEVICES

FIELD OF THE INVENTION

The invention relates generally to the intraluminal delivery of therapeutic devices which includes deploying the devices from delivery vehicles by remote activation of a detachment system closely proximal to the therapeutic device. The disclosure describes apparatuses and methods for accurately and rapidly delivering a therapeutic device at a desired location by applying heat to a thermally-responsive element, resulting in the disengagement of a retention element with the therapeutic device.

BACKGROUND OF THE INVENTION

The use of catheters to insert and position therapeutic devices in the body has become a widely-used form of treatment for various conditions. Such devices are particularly useful in treating areas where traditional procedures are difficult such as in narrow cranial blood vessels. For example, vaso-occlusive devices such as embolic coils or wires are inserted at sites of aneurysm to occlude blood flow. The decreased blood flow reduces the pressure on the aneurysm and reduces the risk of a ruptured aneurysm. The coil also promotes thrombus formation. Embolic coils and wires can assume different shapes to better occlude a blood vessel. The coils can be coated with various materials to improve thrombogenicity. U.S. Pat. No. 6,723,108 describes some of the characteristics of different shapes of embolic coils. This patent and all other patents and patent application publications identified herein are hereby incorporated herein by reference.

Typically, procedures using a catheter involve inserting the distal end of the catheter into the vasculature of a patient and guiding it to a predetermined delivery site. A vascular occlusion device, such as an embolic coil, is attached to the end of a structure capable of manipulating the therapeutic device. This structure may, for example, be used to push the coil through the catheter and out of its distal end into the delivery site. The coil is then released from the pusher. The small size of some blood vessels requires that mechanism that releases the coil from the pusher be simple and not require complicated equipment. In addition, the release mechanism must accurately and rapidly place the therapeutic device at the determined site. Problems that have been associated with the release of the coil include the force of the coil exiting the delivery catheter causing the coil to overshoot the desired site or dislodge previously deployed coils.

In response to the above mentioned concerns, numerous devices and release mechanisms have been developed in an attempt to provide a delivery system which provides a rapid release or detachment mechanism to release the device at the correct location. One such device is disclosed in Geremia et al. U.S. Pat. No. 5,108,407, which shows a fiber optic cable including a connector device mounted to the end to the optic fiber. An embolic coil is attached to the connector device by a heat releasable adhesive. Laser light is transmitted through the fiber optic cable to increase the temperature of the connector device, which melts the adhesive and releases the embolic coil. One drawback to using this type of system is the potential risk of melted adhesives contaminating the blood stream.

Yet another embolic coil positioning and delivery system is described in Saadat et al. U.S. Pat. No. 5,989,242, which discloses a catheter having a shape memory alloy connector attached to the distal end of the catheter. The connector includes a socket having a pair of spaced-apart fingers which are responsive to a change in temperature. The fingers are bent towards each other and hold a ball which is connected to an end of an embolic coil. The connector absorbs laser light transmitted through an optical cable and transforms the light into heat energy. The heat energy raises the temperature of the connector and opens the fingers, thereby releasing the embolic coil. This type of ball and socket connection is rigid and causes the catheter to be stiff, making it difficult to guide the catheter through the vasculature of the body.

U.S. Patent application publication 2005/0113864 A1 by Gandhi et al describes an apparatus for the release and deployment of a therapeutic device where the therapeutic device is secured to the distal end of a pusher by a collar. When heated, the collar alters its configuration and releases the therapeutic device into the vasculature. The collar can be formed from shape memory metals or from thermoplastic polymers. In another embodiment found in the same disclosure, the therapeutic device is secured to the pusher by a connector fiber that can be broken by heating, releasing the therapeutic device. The connector fiber can be formed from a thermoplastic material or a biodegradable material that degrades or decomposes with heating. One difficulty associated with these arrangements is that the material forming the collar or fibre may fragment or dissolve when heated, releasing materials into the bloodstream. The Gandhi et al disclosure addresses this by performing the heating step completely within a catheter such that the pusher and therapeutic device become disengaged within the catheter. This approach is problematic because it may reduce the ability of the pusher to manipulate the therapeutic device to precisely the correct location in the vasculature.

In keeping with the invention, therefore, a need remains for a therapeutic device delivery apparatus which uses material that changes to effect therapeutic device release while remaining totally encapsulated, which has a reliable operating principle and is simple to use but still provides excellent control over the therapeutic device during the process of inserting and releasing it in the vasculature.

SUMMARY OF THE INVENTION

The invention concerns systems and methods for accurate and rapid delivery of a therapeutic device to a desired location in a body of a patient. A decoupling assembly is attached to the distal end of a pusher assembly. The decoupling assembly comprises a retention element and a thermally-responsive element. The thermally-responsive element maintains the retention element in a position where the retention element engages the therapeutic device. When energy is applied to an energy-responsive element, heat is transmitted to the thermally-responsive element and the thermally-responsive element changes its configuration such that the retention element is no longer engaged with the therapeutic device. Consequently, the therapeutic device is released at the desired site;

The energy-responsive element, which can take the form of a so-called heating element, may be heated using a variety of energy sources such as electrical energy, laser light, a radiofrequency source, or ultrasonic energy. The energy from these sources is transmitted to the energy-responsive element through conductors located in, at, or near the pusher element. In an alternative embodiment, energy to heat the energy-responsive element is provided without the use of conductors in, at or near the pusher. Energy from a radiofrequency source is one such energy source that can be transmitted through the body and direct its energy to the delivery device.

A general aspect of the present invention is to provide an apparatus for releasing a therapeutic device into the vasculature and methods for using same.

Another aspect of the invention is to provide devices capable of releasing embolic coils into the vasculature and methods for using such devices.

Other aspects, objects and advantages of the present invention will be understood from the following description according to the preferred embodiments of the present invention, specifically including stated and unstated combinations of the various features which are described herein, relevant information concerning which is shown in the accompanying drawings.

BRIEF DESCRIPTION OF THE DRAWINGS

In describing the preferred embodiments of the present invention, reference will be made to the accompanying drawings, wherein:

FIG. 1 is a sectional view of a therapeutic device delivery apparatus in accordance with a preferred embodiment of the present invention at which the retention element is engaged with an embolic coil;

FIG. 2 is a sectional view of the apparatus in FIG. 1 showing the thermally-responsive member in an altered configuration at which the retention element is no longer engaged with the therapeutic device, resulting in release of the therapeutic device into the vasculature;

FIG. 3 is a sectional view of another embodiment, the delivery device being shown engaged with a therapeutic device;

FIG. 4 is a sectional view of a further embodiment, the delivery device also being shown engaged with a therapeutic device and includes an electrical conductor that transmits energy to the energy-responsive element and the body of the patient acts as a ground;

FIG. 5 is a sectional view of an alternative embodiment of the apparatus with the delivery device also being shown engaged with a therapeutic device and where a fiber optic cable located in the lumen of the pusher transmits laser light to the energy-responsive element; and FIG. 6 is a sectional view of an alternative embodiment of the apparatus where an energy source transmits energy to the energy-responsive element in a "wireless" fashion without requiring the transmittal of energy through elements such as conductors associated in the delivery device.

DESCRIPTION OF THE PREFERRED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

As shown in FIGS. 1-6, the present disclosure provides for systems to deliver a therapeutic device and methods for use such systems. In general, the invention includes a pusher element that has a decoupling assembly located at its distal end. The decoupling assembly includes a retention element that engages the therapeutic device when the device is being guided through the vasculature, typically within a guiding catheter (not shown). A thermally-responsive element maintains the engagement of the retention element with the therapeutic device. When the thermally-responsive element is heated, it assumes an altered configuration such that the retention element is no longer maintained in an engaged position at which it is secured to the therapeutic device. Consequently, the therapeutic device is released at the desired location in the vasculature.

FIGS. 1 and 2 show one embodiment of the invention. In this and the other embodiments disclosed here, the therapeutic device 11 is shown as an embolic coil. A decoupling assembly 12 is attached to the distal end of a pusher element 13 by any suitable approach, such as medical grade adhesive, mechanical attachment such as crimping or embedding or shrink wrapping or tubing, for example. The decoupling assembly comprises a retention element 15, an energy-responsive element 17 and a thermally-responsive element 18.

The retention element 15 is formed from a material that is resilient; that is, the element will move from one configuration to another when permitted and is not susceptible to fracture when stressed or deformed. While shape memory materials such as Nitinol are suitable, it is not necessary that the material have shape memory properties. The retention element may, for example, be manufactured from spring steel or other resilient metals or polymers. As shown in FIG. 1, the retention element 15 may assume an expanded or offset configuration such that its external surface 16 pushes with sufficient force against the inner surface 19 of a therapeutic device 11. This is illustrated in FIG. 1 by the engagement of a turn 22 on an embolic coil by the retention element 15. The engagement of the retention element 15 with the therapeutic device 11 allows the pusher 13 to be used to manipulate the position of the therapeutic device 11. As shown in FIG. 2, the retention element 15, assumes a generally collapsed and somewhat more straight line orientation when not engaging the embolic coil, when compared with the extended or bulbous shape of FIG. 1. The shape illustrated in FIG. 1 is that of a substantially spherical retention element.

The thermally-responsive element 18 is manufactured from a material that is thermally sensitive; that is, it assumes a different configuration when sufficient heat is applied. In its unheated configuration shown in FIG. 1, the thermally-responsive element 18 contacts the retention element 15 and maintains the retention element 15 in its expanded or offset position such that the retention element 15 engages the therapeutic device 11. As a consequence, the desired position of the therapeutic device 11 within the vasculature can be achieved by manipulating the pusher 13.

The thermally-responsive element 18 can be made from a material that deforms, contracts or otherwise alters its configuration when heated. For example, the thermally-responsive element 18 may be formed from a material that changes from a solid to a flowable form, such as a liquid, when heat energy is applied above a selected temperature and a exceeding a selected time period. Suitable materials for the thermally-responsive element include low temperature solder, hot melt adhesives, waxes and low melting point metals. When the thermally-responsive element 18 assumes a liquid form, it is no longer able to maintain the retention element 15 in its expanded configuration and the retention element 15 assumes its collapsed configuration and disengages from the therapeutic device.

The change in form of the thermally-responsive element 18 should not occur spontaneously at body temperature and ideally should only occur when the thermally-responsive element 18 is exposed to heat produced by the energy-responsive element 17. In addition, the amount of heat and the length of exposure to heat produced by the energy-responsive element 17 should not exceed an acceptable level in a surgical context. For example, the heat produced should not cause unwanted adverse reactions in the patient, such as coagulation or denaturing of the blood or undesirable alterations in other tissues.

To ensure the thermally-responsive element 18 remains in its unaltered configuration before heating by the energy-responsive element 17, the thermally-responsive element should change from a solid to a flowable form above a temperature of at least about 40° C. and preferably from at least about 43° C. To reduce the risk of damage to the tissues of a patient, the thermally-responsive element should change its form at a temperature that does not exceed about 50° C. and preferably should not exceed about 47° C. That is, a preferred range for the change of form of the thermally-responsive element is from about 40° C. to 50° C. and a particularly preferred range is 43° C. to 47° C. However, a particular procedure may require different conditions. In such cases, temperatures greater than 50° C. may be acceptable when applied for a shorter time such that there is no significant alteration in tissues of the patient.

It may be necessary to include a membrane or the like to encapsulate a thermally-responsive element when it transforms to a flowable form, depending for example upon the encapsulating capabilities, if any, of the rest of the decoupling assembly. The encapsulating material serves a barrier function. Encapsulation prevents release of the material forming the thermally sensitive material when it is heated. In a preferred embodiment, the thermally-responsive element is encapsulated in a flexible membrane 23. The membrane should be flexible enough to accommodate the collapse of the retention element 15 when the thermally-responsive membrane 23 is heated. The integrity of the membrane 23 should not be compromised at the conditions used to heat the thermally-responsive element 18 to alter its configuration. For example, the membrane 23 should not undergo a phase transition from solid to liquid at the conditions used to heat the thermally-responsive element. A preferred material for the membrane is a silicone.

In the embodiment shown in FIGS. 1 and 2, electrical wires 20, 21 connect with the energy-responsive element which may be considered a heating element. The wires complete a circuit between an electrical energy source (not shown) and the energy-responsive or heating element. The pusher 13 can have a lumen 14 through which wires 20, 21 extend between the electrical energy source and the energy-responsive element 17.

The energy-responsive element 17 and the thermally-responsive element 18 are designed, sized and positioned such that the energy-responsive element 17 helps to transform energy applied to it into heat energy which then is transmitted to the thermally-responsive element 18. As shown in FIG. 2, heat transmitted from the energy-responsive element 17 alters the configuration of the thermally-responsive member 18 such that it no longer maintains the retention element 15 in an expanded, offset position. The retention element moves from an expanded, offset position to a generally collapsed or somewhat straight-line position and disengages from the therapeutic device 11. Consequently, as show in FIG. 2, the therapeutic device 11 is released from the pusher 13 and placed in the vasculature at the desired location.

The retention element can be provided in any number of shapes with the only requirement being that it is capable of engaging the therapeutic device in at least one configuration and disengaging the therapeutic device in another configuration. For example, in the embodiment shown in FIG. 3, decoupling assembly 32 has a retention element 34 shaped such that a portion 35 of the retention element intercalates between the turns 22 of the embolic coil therapeutic device 11. A thermally responsive element 37 is provided in this embodiment. It can be encapsulated within a membrane 31.

In another embodiment, shown in FIG. 4, decoupling assembly 42 includes a thermally-responsive element 46. This is shown with an encapsulating membrane 41. The thermally-responsive element is positioned generally within retention element 44 which has one or more protrusions 45 that intercalate with the turns 22 of the embolic coil therapeutic device 11.

FIGS. 1 and 2 present one embodiment that can be used to deliver electrical energy to the energy-responsive element. In an alternative embodiment shown in FIG. 3, electrical wires 38, 39 are positioned externally on the surface of the pusher 33 and connect the energy source (not shown) and the energy-responsive element or heating 36 to form a circuit. The pusher 33 can be solid. After the application of energy to the energy-responsive or heating element 36, heat is generated and/or transmitted to the thermally-responsive member 37. Heating alters the configuration of the thermally-responsive member 37 and the retention element 34 moves from an expanded, offset position to a generally collapsed position (not shown) in the matter of that shown in FIG. 2 and the retention element disengages from the therapeutic device 11.

In alternative embodiments, energy is provided to the energy-responsive or heating element through different means and using different types of energy sources. For example, as shown in FIG. 4, the pusher 47 is formed, at least in part, from a material that conducts electricity. In this embodiment, the pusher 47 is in communication with the energy-responsive or heating element 49. A support sheath 43 is shown surrounding all but the distal end portion of the pusher 47 and the energy-responsive or heating element 49. An electrical circuit develops with the body performing the function of an electrical ground. In a preferred embodiment, the pusher 47 and energy-responsive or heating element 45 are formed from the same piece of material. Alternatively, the element 45 is manufactured from a separate piece of material and attached to the distal end of the pusher 47 by means known in the art. The embodiment that employs a unitary construction for the pusher is preferred for its simplicity and reduced chance of failure due to improper attachment of the pusher 47 and energy-responsive or heating element 49.

In another embodiment, the energy-responsive or heating element is heated by light energy, preferably laser light. As shown in FIG. 5, pusher 53 includes a fibre optic cable 57 in a lumen thereof for transmitting light from a laser light source (not shown) to the energy-responsive or heating element 55 found in the decoupling assembly 52. The element 55 receives the light energy, transforms same into heat energy which is then transmitted to the thermally-responsive element 56, shown encapsulated in a membrane 51. As a consequence of transmittal of heat, the thermally-responsive element 56 assumes its altered configuration. As a result, the retention element 54 moves from an expanded, offset position to a generally collapsed or somewhat more straight-line position similar to that of FIG. 2 so the retention element 54 disengages from the therapeutic device 11.

Alternatively, the pusher may contain materials that conduct ultrasonic energy from an ultrasonic energy source (not shown). The ultrasonic energy conductor may be placed in the lumen of the pusher. In this approach, the energy responsive element 55 transforms the ultrasonic energy to thermal energy to collapse the thermally-responsive element 56.

In the embodiment shown in FIG. 6, an external energy source 67 heats the energy-responsive element 65 without the use of energy-conducting elements in the pusher 63 or decoupling assembly 62. In this embodiment, energy is directly transmitted to the 65 from the external energy source 67 through the body of the patient, including through the vasculature 68.

Typically, energy source 67 is a radiofrequency (RF) source of the type generally known in the art. As in previous embodiments, heat alters the configuration of the thermally-responsive element 66 (shown encapsulated in membrane 61) such that it no longer maintains the retention element 64 in an expanded, offset position. The retention element 64 moves from an expanded, offset position to a generally collapsed or somewhat more straight-line position along the lines of FIG. 2 and disengages from the therapeutic device 11.

It will be understood that the embodiments of the present invention which have been described are illustrative of some of the applications of the principles of the present invention. Numerous modifications may be made by those skilled in the art without departing from the true spirit and scope of the invention. Various features which are described herein can be used in any combination and are not limited to procure combinations that are specifically outlined herein.

The invention claimed is:

1. An system for the endoluminal delivery of a therapeutic device, comprising:
   a therapeutic device having a proximal end portion and a distal end portion;
   a pusher element sized and shaped for intraluminal delivery, said pusher element having a distal end portion;
   a decoupling assembly attached to said distal end portion of said pusher, said decoupling assembly including an energy-responsive element;
   said decoupling assembly including a retention element having an offset orientation at which the retention element retains said therapeutic device, said retention element also having a generally collapsed orientation;
   said decoupling assembly further including a thermally-responsive element having an expanded configuration that maintains said retention element in said offset orientation and having an altered configuration that does not maintain said retention element in said offset orientation;
   said thermally-responsive element, retention element and energy-responsive element are designed, sized and shaped relative to each other such that said thermally-responsive element assumes said altered configuration when energy is transmitted to said energy-responsive element and said retention element moves to its said collapsed orientation and no longer retains said therapeutic device; and
   a membrane encapsulating said thermally-responsive element.

2. The system of claim 1, wherein said therapeutic device is an embolic coil.

3. The system of claim 1, wherein said thermally-responsive element is formed from a material that changes its form when heated to a temperature of at least about 40° C.

4. The system of claim 1, wherein said thermally-responsive element is formed from a material that changes its form at when heated to a temperature of from about 40° C. to about 50° C.

5. The system of claim 1, wherein said energy-responsive element is heated by an energy source selected from the group consisting of electrical, laser light, ultrasonic or radiofrequency.

6. The system of claim 1, wherein said pusher is electrically conductive and wherein said pusher is in communication with said energy-responsive element.

7. The system of claim 1, wherein said pusher member further comprises a lumen, and wherein electrical wires are disposed within said lumen and said wires are in communication with said energy-responsive element and said energy source.

8. The system of claim 1, wherein a fibre optic cable is disposed within a lumen of the pusher member and said cable is in communication with said energy-responsive element and said energy source.

9. The system of claim 1, further including an ultrasonic conductor in communication with said energy-responsive element and said energy source.

10. The system of claim 1, wherein said energy-responsive element is heated by energy transmitted in wireless fashion to said energy-responsive element through the body of a patient.

11. The apparatus of claim 1, wherein said thermally-responsive element is formed from a material selected from the group consisting of low temperature solder, hot melt adhesives, waxes and low melting point metals.

12. A decoupling assembly for engagement and release of a therapeutic device, comprising:
    an energy-responsive element;
    a retention element having an offset orientation that maintains a therapeutic device and has a generally collapsed orientation;
    a thermally-responsive element having an expanded configuration that maintains said retention element in said offset orientation and having an altered configuration that does not maintain said retention element in said offset orientation;
    said thermally-responsive element, retention element and energy-responsive element are sized and shaped relative to each other such that said thermally-responsive element assumes said altered configuration when energy is transmitted to said energy-responsive element and said retention element moves to its said collapsed orientation; and
    said thermally-responsive element is formed from a material selected from the group consisting of low temperature solder, hot melt adhesives, waxes and low melting point metals.

13. The system of claim 12, further comprising a membrane encapsulating said thermally-responsive element.

14. The apparatus of claim 12, further including a material encapsulating said thermally-responsive element.

15. The apparatus of claim 12, wherein said retention element is formed from a resilient material.

16. The apparatus of claim 12, wherein said thermally-responsive element is formed from a material that changes its form when heated to a temperature of at least about 40° C.

17. The apparatus of claim 12, wherein said thermally-responsive element is formed from a material that changes its form when heated to a temperature of from about 40° C. to about 50° C. and above.

18. The apparatus of claim 12, wherein said thermally-responsive element is formed from a material that changes its form when heated to a temperature of from about 43° C. to about 47° C.

19. An system for the endoluminal delivery of a therapeutic device, comprising:
    an embolic coil therapeutic device having a proximal end portion and a distal end portion;
    a pusher element sized and shaped for intraluminal delivery, said pusher element having a distal end portion;
    a decoupling assembly attached to said distal end portion of said pusher, said decoupling assembly including an energy-responsive element;

said decoupling assembly including a retention element having an offset orientation at which the retention element retains said therapeutic device, said retention element also having a generally collapsed orientation;

said decoupling assembly further including a thermally-responsive element having an expanded configuration that maintains said retention element in said offset orientation and having an altered configuration that does not maintain said retention element in said offset orientation;

said thermally-responsive element, retention element and energy-responsive element are designed, sized and shaped relative to each other such that said thermally-responsive element assumes said altered configuration when energy is transmitted to said energy-responsive element and said retention element moves to its said collapsed orientation and no longer retains said therapeutic device; and said thermally-responsive element is formed from a material selected from the group consisting of low temperature solder, hot melt adhesives, waxes and low melting point metals.

20. The system of claim 19, wherein said thermally-responsive element is formed from a material that changes its form at when heated to a temperature of from about 40° C. to about 50° C.

21. The system of claim 19, wherein said energy-responsive element is heated by an energy source selected from the group consisting of electrical, laser light, ultrasonic or radio frequency.

22. The system of claim 19, wherein said pusher is electrically conductive and wherein said pusher is in communication with said energy-responsive element.

23. The system of claim 19, wherein said pusher member further comprises a lumen, and wherein electrical wires are disposed within said lumen and said wires are in communication with said energy-responsive element and said energy source.

24. The system of claim 19, wherein a fibre optic cable is disposed within a lumen of the pusher member and said cable is in communication with said energy-responsive element and said energy source.

25. The system of claim 19, further including an ultrasonic conductor in communication with said energy-responsive element and said energy source.

26. The system of claim 19, wherein said energy-responsive element is heated by energy transmitted in wireless fashion to said energy-responsive element through the body of a patient.

27. A decoupling assembly for engagement and release of a therapeutic device, comprising:

an energy-responsive element;

a retention element having an offset orientation that maintains a therapeutic device and has a generally collapsed orientation;

a thermally-responsive element having an expanded configuration that maintains said retention element in said offset orientation and having an altered configuration that does not maintain said retention element in said offset orientation;

said thermally-responsive element, retention element and energy-responsive element are sized and shaped relative to each other such that said thermally-responsive element assumes said altered configuration when energy is transmitted to said energy-responsive element and said retention element moves to its said collapsed orientation; and a material encapsulating said thermally-responsive element.

28. The apparatus of claim 27, wherein said retention element is formed from a resilient material.

29. The apparatus of claim 27, wherein said thermally-responsive element is formed from a material that changes its form when heated to a temperature of from about 40° C. to about 50° C. and above.

30. The apparatus of claim 27, wherein said thermally-responsive element is formed from a material that changes its form when heated to a temperature of from about 43° C. to about 47° C.

* * * * *

UNITED STATES PATENT AND TRADEMARK OFFICE
CERTIFICATE OF CORRECTION

| | | |
|---|---|---|
| PATENT NO. | : 7,582,101 B2 | Page 1 of 1 |
| APPLICATION NO. | : 11/363775 | |
| DATED | : September 1, 2009 | |
| INVENTOR(S) | : Jones et al. | |

It is certified that error appears in the above-identified patent and that said Letters Patent is hereby corrected as shown below:

On the cover page,

Item [*] Notice:   Subject to any disclaimer, the term of this patent is extended or adjusted under 35 USC 154(b) by (599) days Delete the phrase "by 599 days" and insert -- by 784 days --

Signed and Sealed this

Twentieth Day of April, 2010

David J. Kappos
*Director of the United States Patent and Trademark Office*